(12) United States Patent
Tavger

(10) Patent No.: US 6,283,936 B1
(45) Date of Patent: Sep. 4, 2001

(54) APPARATUS AND METHOD FOR CLEANSING TISSUE

(75) Inventor: Michael Tavger, Katzrin (IL)

(73) Assignee: Tav-Tech Ltd., Katzrin (IL)

( * ) Notice: Subject to any disclaimer, the term of this patent is extended or adjusted under 35 U.S.C. 154(b) by 0 days.

(21) Appl. No.: 09/194,044

(22) PCT Filed: Jan. 22, 1997

(86) PCT No.: PCT/IL97/00027
§ 371 Date: Nov. 18, 1998
§ 102(e) Date: Nov. 18, 1998

(87) PCT Pub. No.: WO98/01181
PCT Pub. Date: Jan. 15, 1998

(30) Foreign Application Priority Data

Jul. 5, 1996 (IL) ............................................. 118801
Jan. 16, 1997 (IL) ............................................. 120021

(51) Int. Cl.⁷ .................................................. A61M 37/00
(52) U.S. Cl. ................................ 604/24; 604/35; 604/290
(58) Field of Search ............................ 604/28, 30, 31, 604/35, 140, 24, 289, 290, 26, 23, 22; 222/135, 394, 407.7; 137/614.18, 616.3, 825; 239/574; 433/80, 88–90

(56) References Cited
U.S. PATENT DOCUMENTS 4,462,394 * 7/1984 Jacobs ............................... 606/192 X
5,022,414 * 6/1991 Muller ............................... 606/190 X
5,419,310 * 5/1995 Frassica et al. ....................... 600/121
5,554,111 * 9/1996 Morrey et al. ....................... 604/35 X

* cited by examiner

*Primary Examiner*—Anhtuan T. Nguyen
(74) *Attorney, Agent, or Firm*—Fay, Sharpe, Fagan, Minnich & McKee, LLP

(57) ABSTRACT

An apparatus employing liquid and gas as working fluids for cleansing living tissue includes a container for a sterile liquid and a fluid delivery head having a liquid entry port, a gas entry port, a fluid outlet apparatus and a valve located between the entry ports and the fluid outlet apparatus. The valve selectively permits respective liquid and gas flows from the entry ports to the fluid outlet apparatus. A liquid conduit extends between a liquid inlet located within the container and a liquid outlet connected to the liquid entry port of the delivery head. A gas conduit extends between a gas inlet and a gas outlet. The gas inlet is connected to a source of pressurized gas and the gas outlet is connected to the gas entry port of the delivery head. The gas conduit is connected to the container via an intermediate outlet port. Also provided is an apparatus for selectively exposing the source of sterile liquid to a flow pressurized gas flowing from the gas inlet to the gas outlet and into the gas entry port of the fluid delivery head in order to pump the sterile liquid along the liquid conduit from the inlet to the outlet and into the liquid entry port of the fluid delivery head.

13 Claims, 5 Drawing Sheets

APPARATUS AND METHOD FOR CLEANSING TISSUE

FIELD OF THE INVENTION

The present invention relates to the treatment of living tissue, in general, and to the cleansing of exposed living tissue, in particular.

BACKGROUND OF THE INVENTION

The cleansing of exposed in vivo tissue, such as of humans or animals during surgical procedures, requires the removal from the tissue of solid contaminants, such as fibers, dust, sand particles, and the like, and organic matter, such as puss, fats, and so on. Organic matter tends to be fastened to the tissue much more strongly than the non-organic matter, and is thus more difficult to remove therefrom. Accordingly, while non-organic matter may be cleansed from the tissue by means of a liquid stream, it is often not possible to remove some organic matter in this way. More specifically, and most problematic, are those particles which are smaller than the thickness of the boundary layer of the fluid stream which is formed on the tissue; the boundary layer being characterized by having a fluid velocity which reduces sharply adjacent to the flow surface, and which is zero at the surface.

The smallest particles, which are located in the boundary layer, exhibit drag resistance of a magnitude that is sufficient for them to stay affixed to the surface and not to be swept away by the fluid stream, even if this has a very high velocity.

In an attempt to solve this problem, there have been developed a number of prior art devices which employ pulsed washing streams, such as described in U.S. Pat. Nos. 4,350,158 and 4,982,730. These pulsed stream devices operate on the basis of providing a liquid stream with a reduced boundary layer thickness, in order to sweep away small particles. These devices, however, generally have complicated constructions, use very large quantities of liquid, and have been found to provide only a small improvement over non-pulsed devices.

SUMMARY OF THE INVENTION

The present invention seeks to provide a method of and apparatus for cleansing living tissue, such as during surgical procedures on humans and animals, and which overcome disadvantages of known art.

More specifically, it is sought to provide a cleansing method and apparatus which apply to the tissue surface a sterile liquid in a manner which is capable of removing even very small contaminants, thereby providing more effective cleansing of tissue than known in the art.

Furthermore, the cleansing is performed using relatively small amounts of liquid, thereby being not only more efficient and less wasteful than known methods, but also being more convenient and less messy to use than known methods.

The method of the invention is further characterized by having a therapeutic effect on the tissue being cleansed.

There is thus provided, in accordance with a preferred embodiment of the invention, apparatus employing liquid and gas as working fluids for cleansing living tissue, which includes:
  a container for a sterile liquid;
  a fluid delivery head having a liquid entry port and a gas entry port, fluid outlet apparatus, and valve apparatus located between the entry ports and the fluid outlet apparatus and for selectably permitting respective liquid and gas flows from the entry ports to the fluid outlet apparatus;
  liquid conduit apparatus extending between a liquid inlet located within the container and a liquid outlet connected to the liquid entry port of the delivery head;
  gas conduit apparatus extending between a gas inlet and a gas outlet, wherein the gas inlet is connected to a source of pressurized gas and the gas outlet is connected to the gas entry port of the delivery head, and wherein the gas conduit apparatus is connected to the container via an intermediate outlet port; and
  apparatus for selectably exposing the source of sterile liquid to a flow of pressurized gas flowing from the gas inlet to the gas outlet and into the gas entry port of the fluid delivery head, thereby to pump the sterile liquid along the liquid conduit apparatus, from the inlet to the outlet, and into the liquid entry port of the fluid delivery head,
  wherein the fluid outlet apparatus comprises a gas-liquid combining member arranged to receive the gas and liquid flows and to combine them into a gas-liquid outflow which is operative to exit the apparatus through the fluid outlet in the form of a sterile liquid mist suspended in a high velocity gas stream.

Additionally in accordance with a preferred embodiment of the invention, the gas flow exits the valve apparatus into the gas-liquid combining member at a pressure of a first magnitude, and the combining member is operative to cause a pressure drop in the gas flow therethrough such that the pressure of the gas-liquid outflow downstream of the fluid outlet, is of a second magnitude, wherein the first magnitude is at least twice the second magnitude, so as to cause a shock wave in the gas-liquid flow downstream of the fluid outlet and atomizing of the liquid portion of the outflow into microscopic droplets, thereby to form a mist suspended in the gas portion of the outflow.

Further in accordance with a preferred embodiment of the invention, the fluid outlet apparatus also includes apparatus for applying a suction force to the tissue being cleansed.

Additionally in accordance with a preferred embodiment of the invention, the fluid outlet apparatus further includes an interior nozzle member arranged to provide an outflow of sterile liquid, and the nozzle member includes:

a rear portion configured to fit over the interior nozzle member and arranged to fit over the interior nozzle member so as to define a passageway therebetween for the gas flow;

a waist portion defined by a forward tapering of the rear portion;

a front portion defining an opening and tapering rearwardly towards the waist portion, wherein the passageway is formed so as to be increasingly constricted towards the front portion of the nozzle, such that the gas flow passing through the passageway is accelerated to at least sonic velocity, and wherein the front portion widens towards the opening thereof such that the accelerated gas flow expands and thus undergoes a drop to a pressure which is subatmospheric, such that, when the nozzle opening is brought close to tissue contaminated by pollutant particles, the particles are exposed to the subatmospheric pressure so as to be loosened thereby from the tissue.

Preferably, the gas-liquid outflow, downstream of the fluid outlet, has a near-sonic velocity.

Further in accordance with a preferred embodiment of the invention, the gas inlet of the gas conduit apparatus is constructed for connection to a pressurized oxygen source, and the outflow is an outflow of the sterile liquid mist suspended in a high velocity oxygen stream.

In accordance with a further preferred embodiment of the invention, there is provided a method of cleansing living tissue, which includes:

exposing a source of sterile liquid to a flow of pressurized gas, thereby to cause a pumped supply thereof into a fluid delivery head;

supplying the pressurized gas to the fluid delivery head;

combining the gas and liquid supplied to the delivery head so as to provide a gas-liquid outflow in the form of a sterile liquid mist suspended in a high velocity gas stream; and exposing the living tissue to the gas-liquid outflow, thereby to remove therefrom contaminants.

Additionally in accordance with a preferred embodiment of the invention, the step of supplying the pressurized gas includes supplying the gas at a pressure of a first magnitude, and the step of combining includes causing a pressure drop in the gas flow such that the pressure of the gas-liquid outflow, is of a second magnitude, wherein the first magnitude is at least twice the second magnitude, so as to cause a shock wave in the gas-liquid outflow and atomizing of the liquid portion of the outflow into microscopic droplets, thereby to form a mist suspended in the gas portion of the outflow.

Further in accordance with a preferred embodiment of the invention, the method also includes, prior to the step of combining, providing a gas outflow; causing an expansion of the gas outflow, thereby to cause a reduction in the pressure thereof to subatmospheric pressure, thereby provide a suction force; and providing a liquid outflow in conjunction with the expanded gas outflow.

In accordance with yet a further preferred embodiment of the invention, there is provided a method of cleansing and healing damaged living tissue, which includes:

exposing a source of sterile liquid to a flow of pressurized oxygen, thereby to cause a pumped supply thereof into a fluid delivery head;

supplying the pressurized oxygen to the fluid delivery head;

combining the oxygen and liquid supplied to the delivery head so as to provide a oxygen-liquid outflow in the form of a sterile liquid mist suspended in a high velocity oxygen stream; and exposing the damaged tissue to the oxygen-liquid outflow, thereby to remove contaminants from the tissue, to prevent its drying out, and to cause healing thereof.

BRIEF DESCRIPTION OF THE DRAWINGS

The present invention will be more easily understood and appreciated from the following detailed description, taken in conjunction with the drawings, in which.

DETAILED DESCRIPTION OF A PREFERRED EMBODIMENT

Figure 1:
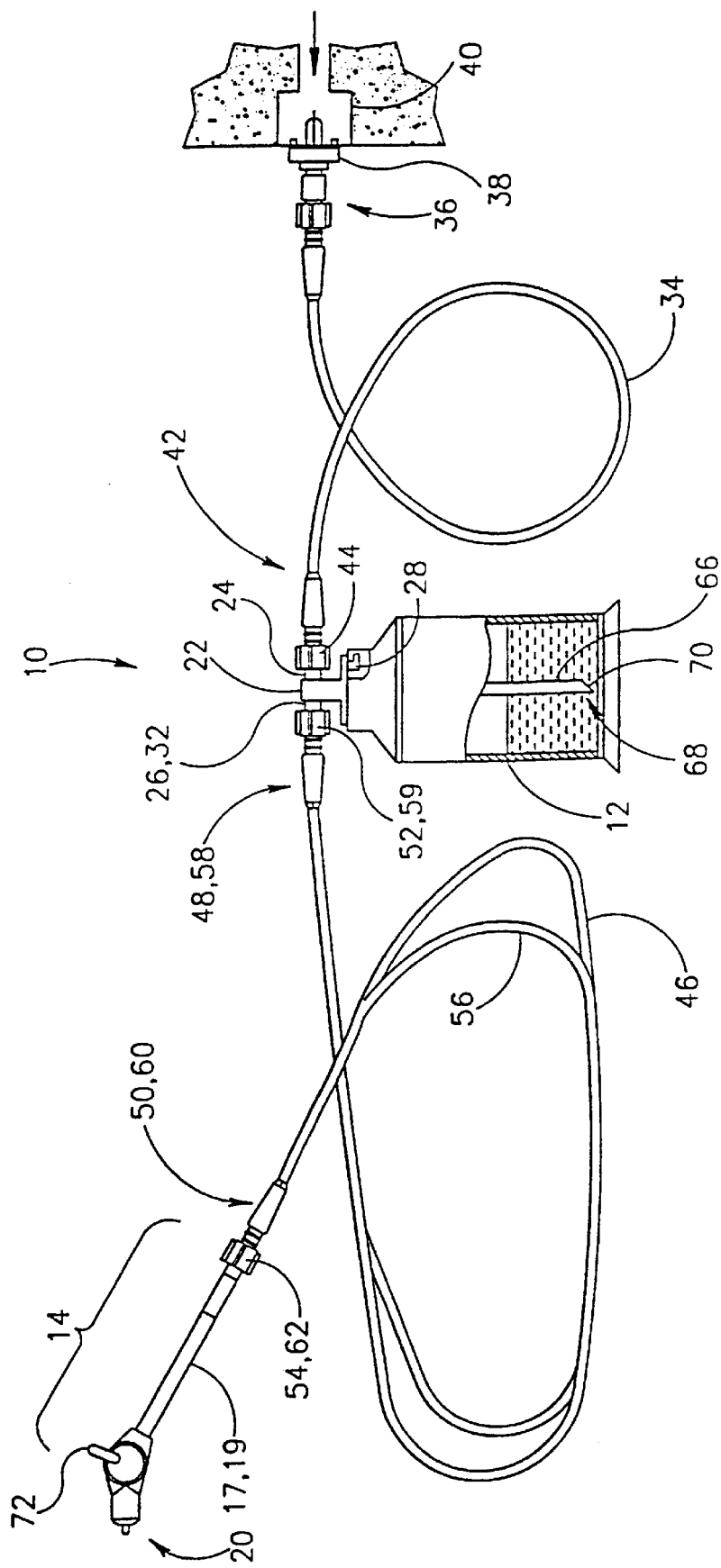
FIG. 1 is a general view of the liquid-gas apparatus of the present invention.

Referring now to FIG. 1, the present invention provides apparatus, referenced generally 10, which employs liquid and gas as working fluids for cleansing living tissue, such as human or animal tissue during surgical procedures. It will be appreciated from the following description that the present apparatus is characterized by being highly efficient for the removal of contaminant particles from living tissue, including very small particles which cannot be removed by previously known methods. The present apparatus further uses relatively small quantities of liquid, and thus, while serving to cleanse tissue and to prevent it from becoming dry during surgical procedures, it does not create accumulations of large quantities of liquid in the operating area. The use of oxygen, moreover, has therapeutic effects, which are well known, per se. In addition, the use of oxygen as a gas source renders the apparatus useful not only in the operating room, but in any hospital facility having a standard oxygen supply outlet.

Figure 3A:
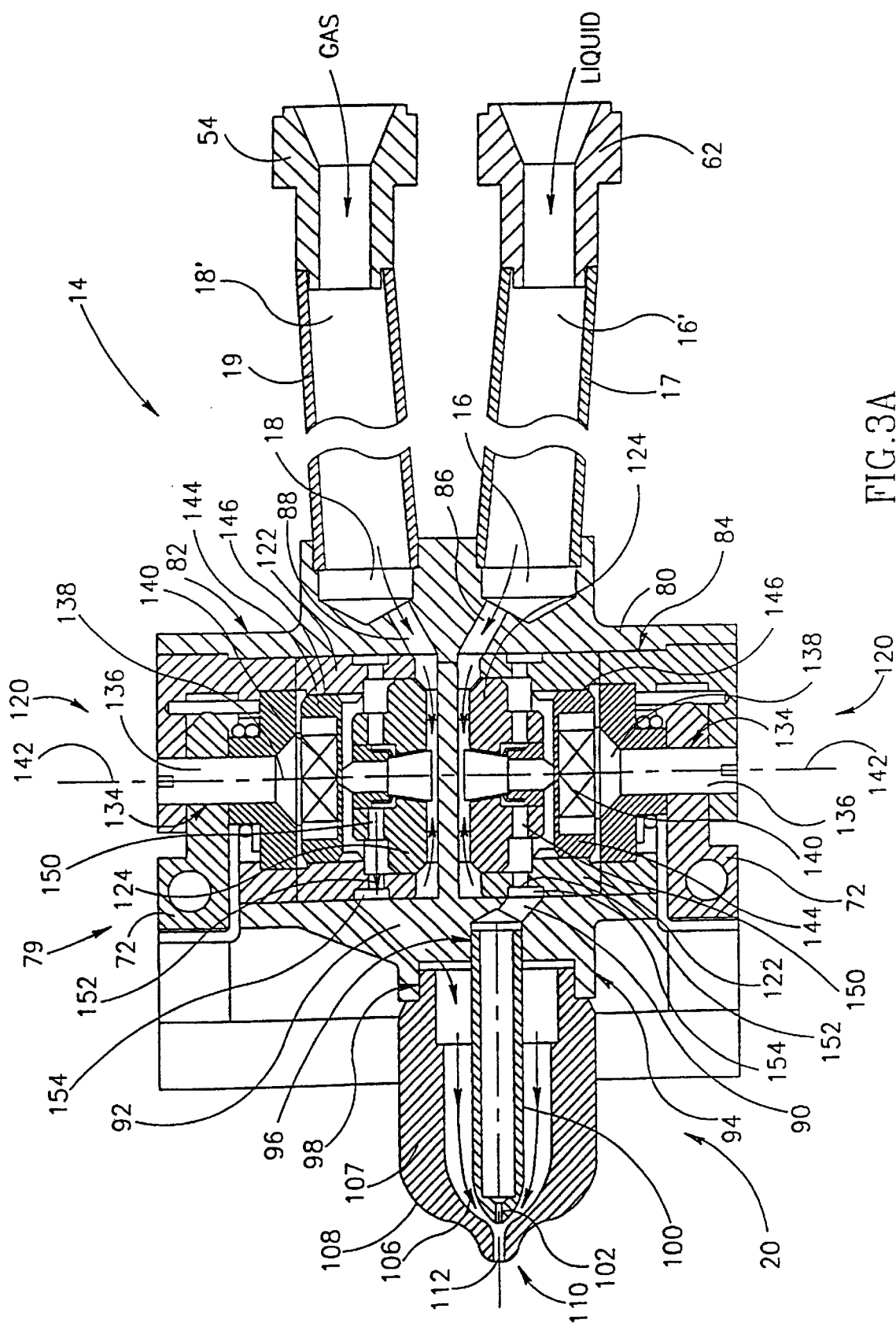
FIG. 3A is a detailed cross-sectional view of the fluid delivery head seen in FIG. 1, when in use.

Apparatus 10 includes a container 12 for containing a supply of a sterile liquid, such as any suitable saline solution, such as a 0.9% sodium chloride solution suitable for irrigation, and a fluid delivery head 14. Referring now also to FIG. 3A, head 14 has a liquid entry port 16, a gas entry port 18, and fluid outlet apparatus 20, via which a gas and liquid mist outflow is provided, at near sonic velocity. It is this outflow which is used for cleansing as described below.

Figure 2B:
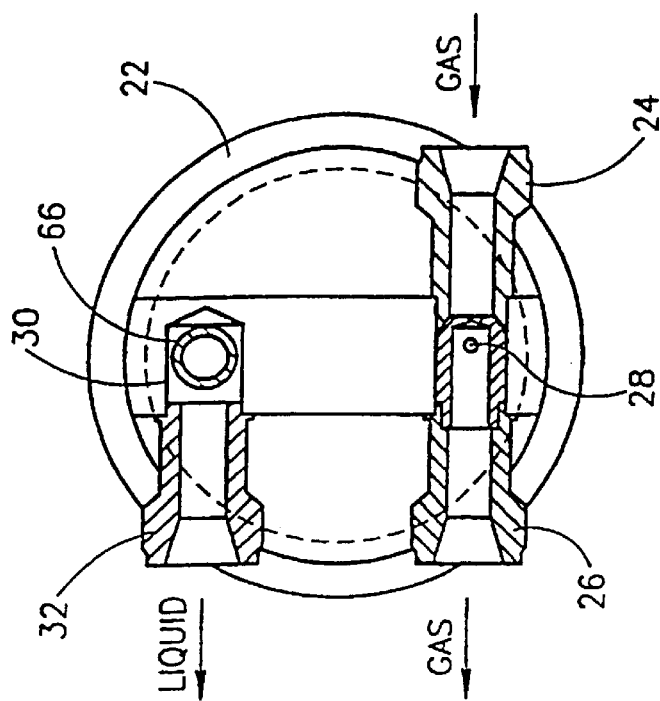
FIG. 2B is an enlarged cross-sectional view of the distributor cap of the container of FIG. 2A, taken along line B—B therein.
Figure 2A:
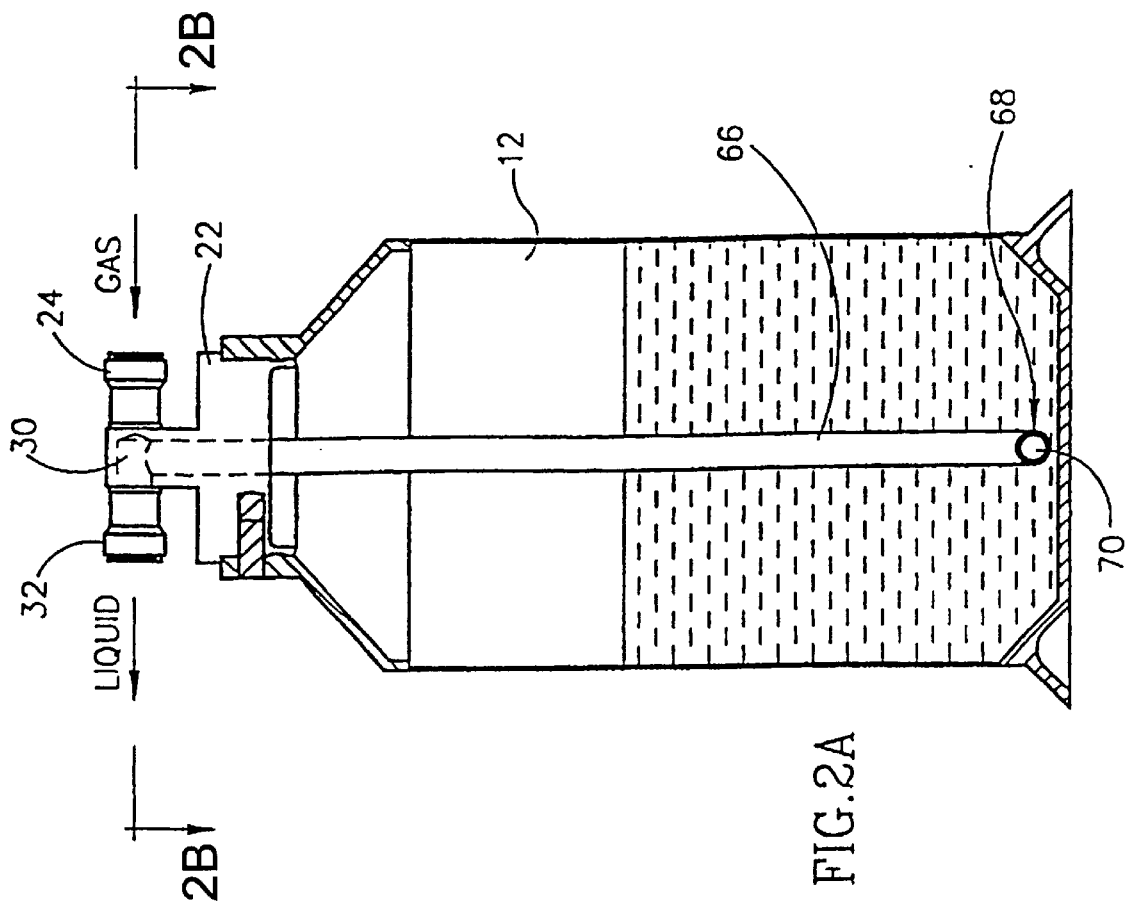
FIG. 2A is an enlarged, part-sectional side view of the container seen in FIG. 1.

By way of example, container 12 may be closed by means of a five-way distributor cap 22, which is fastened to the container as by means of a screw thread (not shown), or by a snap-type or other suitable coupling. Referring now also to FIGS. 2A and 2B, distributor cap 22 has a gas inlet port 24, first and second gas outlet ports, respectively referenced 26 and 28 (FIGS. 1 and 2B), a liquid inlet port 30, and a liquid outlet port 32.

A first gas conduit 34 has an inlet end 36, which is preferably removably coupled, via an oxygen plug 38, to an oxygen outlet 40, together defining a connection such as the "Silberman 2000" oxygen connection, well known and found in many hospitals in Israel and worldwide, and which has associated therewith a central, high pressure oxygen supply. Preferably, the oxygen supply has a generally steady, non-pulsating pressure head, of approximately 3 atm. First gas conduit 34 also has an outlet end 42 which is attached, via a suitable screw or snap coupling 44, to gas inlet port 24. A second gas conduit, referenced 46, has an inlet end 48 and an outlet end 50. Inlet end 48 is attached, via a coupling 52, similar to coupling 44, to first gas outlet port 26, and outlet end 50 is attached, via suitable coupling 54, also similar to coupling 44, to an entry port 18' of a secondary gas conduit 19, coupled to gas entry port 18 of delivery head 14, as shown in FIG. 3A.

A liquid conduit 56 has an inlet end 58 which is attached, via a coupling 59, similar to coupling 44, to liquid outlet port 32 of distributor cap 22, and, further, has an outlet end 60 which is attached, as by a suitable coupling 62, also similar to coupling 44, to an entry port 16' of a secondary liquid conduit 17, coupled to liquid entry port 16 of delivery head 14, as shown in FIG. 3A.

A further tube portion, referenced 66, (FIGS. 1 and 2A) is attached to liquid inlet port 30 of distributor cap 22, and has a free end 68, extending towards the floor of container 12, and which defines a liquid inlet 70.

As seen in FIGS. 2A and 2B, distributor cap 22 is formed such that gas inlet port 24 is connected with first and second gas outlet ports 26 and 28, thereby to facilitate a flow of gas from first gas conduit 34 (FIG. 1), through cap 22, and into second gas conduit 46 (FIG. 1), while also facilitating a pressurized supply of gas into container 12, via second gas outlet port 28. Liquid inlet port 30 and liquid outlet port 32 are also connected to each other, as seen, although the gas and liquid flows through the distributor cap 22 are kept separate.

It will thus be appreciated that, when gas flow through the first and second gas conduits 34 and 46 is permitted, by appropriate adjustment of thumb-operated levers 72 of delivery head 14 (described below), a portion of the pressurized gas enters container 12 via second gas outlet port 28, thereby to pressurize the liquid in the container. This increase in pressure, coupled with a pressure difference between the interior of the container and the outlet apparatus 20 of the delivery head 14, causes an outflow of liquid from the container, into liquid inlet 70 of tube portion 66, and thus also into liquid conduit 56. As will be appreciated from the description of FIGS. 3A–3C below, the pressure just downstream of fluid outlet apparatus 20 is atmospheric, thereby providing a required pressure drop, and thus enabling the described liquid outflow to occur. Preferably, levers 72 are linked by any suitable means (not shown), so as to be operable simultaneously.

Figure 3B:
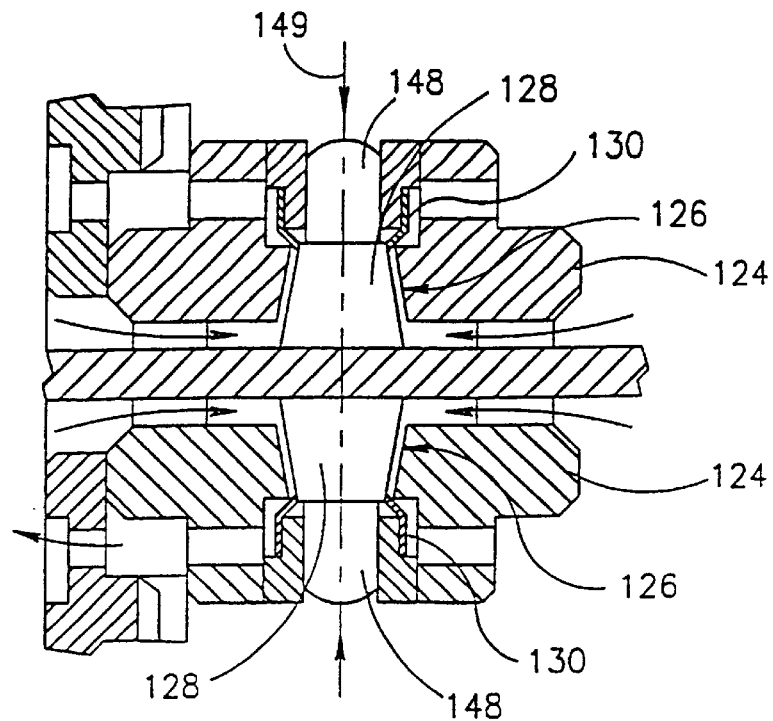
FIG. 3B is an enlarged detailed illustration of a portion of the valve mechanisms, in open positions.
Figure 3C:
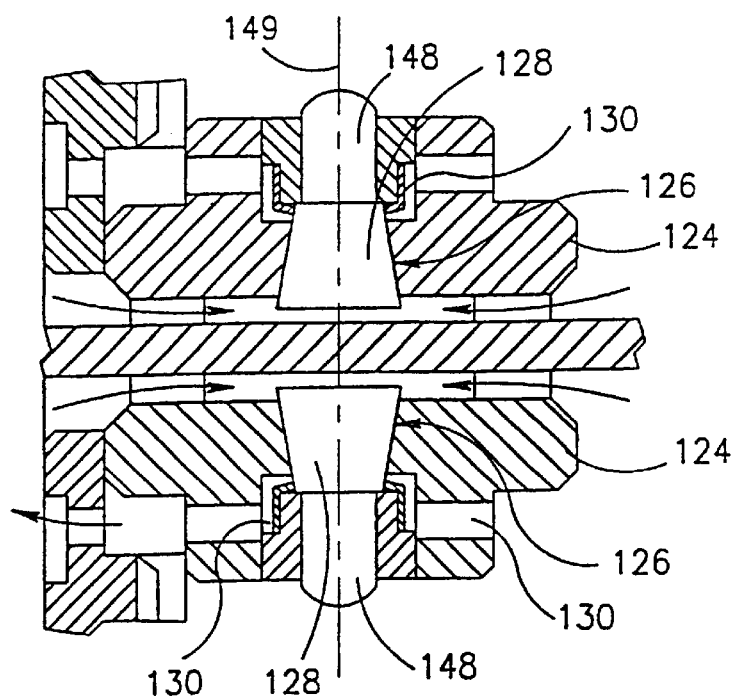
FIG. 3C is an enlarged detailed illustration of a portion of the valve mechanisms, in closed positions.

Reference is now made to FIGS. 3A, 3B and 3C, in which the fluid delivery head 14 (FIG. 3A) and portions of the valve mechanisms thereof (FIGS. 3B and 3C) are shown in detail. As described above, delivery head 14 has a liquid entry port 16, a gas entry port 18, and fluid outlet apparatus 20, via which a gas and liquid mist outflow is provided, at near sonic velocity.

It will be appreciated by persons skilled in the art that the construction of the fluid delivery head 14, as described below in conjunction with FIGS. 3A–3C, is by way of example only, and other suitable types of connections and valves may be used, also in accordance with the invention.

Fluid delivery head 14 includes a valve assembly, referenced generally 79, which facilitates passage of liquid and gas, respectively, from liquid entry port 16 and gas entry port 18, to a gas and liquid combining nozzle member 108, described below. Valve construction 79 includes a body 80 which has formed, in a rear portion thereof, liquid entry port 16 and gas entry port 18. Body 80 further includes laterally positioned liquid and gas valve chambers, respectively referenced 82 and 84, and which are separated from each other, but which are connected with respective entry ports 16 and 18 via a first liquid supply bore 86 and a first gas supply bore 88. Valve chambers 82 and 84 are also connected, via respective second liquid supply bore 90 and second gas supply bore 92, to a front portion of body 80, referenced generally 94.

Front body portion 94 has formed thereon an inner recessed portion 96, and an outer recessed portion 98, which surrounds inner recessed portion. Inner recessed portion 96 communicates with second liquid supply bore 90, and outer recessed portion communicates with second gas supply bore 92. An inner nozzle member 100 is seated within inner recessed portion 96 so as to be contiguous with second liquid supply bore 90, and terminates in a narrow bore front nozzle opening 102, through which a narrow jet of liquid is emitted. A cylindrical, gas-liquid combining member 108 is mounted within outer recessed portion 98 concentric with surrounding inner nozzle member 100.

Combining member 108 has a front portion, indicated generally 110, which is formed so as to converge towards an opening 112, which, as seen, is generally coaxial with nozzle opening 102 of inner nozzle member 100. Combining member 108 is configured so as to cause a central conversion of the gas throughflow in head 14 towards the liquid jet emerging from front nozzle opening 102. Accordingly, as the liquid jet and the gas flow converge upon each other, they become combined into a single gas and liquid jet in the front portion 110 of combining member 108.

Each of valve chambers 82 and 84 contains a valve mechanism, having a construction typically as described below. As these typical valve mechanisms are identical to each other, they are both indicated by reference numeral 120, and the components common to both valve mechanisms are indicated by similar reference numerals. Each valve mechanism 120 has a cylindrical seating member 122, in which is located an inner valve plate 124.

Referring now also to FIGS. 3B and 3C, it is seen that, in the present example, valve plate 124 has a generally conical, outwardly tapering valve opening 126 in which is seated a conical valve element 128. Valve element 128 is maintained, in the absence of any opposing forces, in a retracted, sealed position within opening 126, as shown in FIG. 3C, by means of resilient tension means 130, such as a tension spring. Each thumb controlled lever 72 (FIGS. I and 3A) has a transversely extending threaded bore 134 (FIG. 3A) formed therein. As seen in FIG. 3A, a screw element 136 extends through bore 134 and terminates in a thickened end portion 138. A nut member 140 is connected to end portion 138, and is arranged for free rotation relative thereto, about the longitudinal axis 142 of screw element 136. Nut member 140 is seated in a piston-type casing 144 which is arranged for axial movement along inward-facing tracks 146 formed in seating member 122.

In the position shown in FIG. 3C, it is seen that valve opening 126 is closed by valve element 128. Rotation of lever 72 in a predetermined direction is operative to cause an inward, linear translation of screw element 136. As nut member 140 is free to rotate about axis 142, it does not sustain any rotational moment, and is merely depressed inward by screw element 136. This inward movement causes a corresponding inward movement of casing 144 along tracks 146, which acts on a rear extension 148 of valve element 128 so as to depress it inwards, as shown by arrows 149 in FIG. 3B, thereby to cause a partial opening of valve opening 126, and enabling a throughflow of gas or liquid.

Valve plate 124 has a plurality of first radial bores 150 formed in a rear portion thereof, which communicate with the interior of valve seating member 122. Valve seating member 122 has one or more second radial bores 152, which communicate with an exterior recess 154.

The recesses 154 and the second liquid and gas supply bores 90 and 92 are formed such that opening of valve openings 126 enables respective throughflows of liquid and gas along flow paths constituted by valve openings 126, first radial bores 150 of valve plate 124, second radial bores 152 of valve seating member 122, recesses 154, and either of the supply bores 90 or 92.

As described above, the gas is pressurized, and is supplied at a steady pressure of 2–3 atm. While there may be a minimal head loss during flow through delivery head 14, the delivery head 14 is constructed so as to minimize such head loss, and so as to ensure that the fluid pressure remains in excess of 2 atm, until the point where the combined jet emerges through opening 112 of combining member 108, into the atmosphere.

It will be appreciated by persons skilled in the art that, as the combined fluid jet emerges into atmospheric pressure, it undergoes an instantaneous pressure drop, from 2 atm or more, to 1 atm. A sudden pressure drop of this magnitude results in a velocity of the combined jet at the point of emergence into the atmosphere that approximates the velocity of sound, namely, 330 m/s., and in the production of a shock wave in the jet. The effect of the shock wave is to atomize the liquid fraction of the combined jet into microscopic water droplets, such that there is obtained a jet consisting of a liquid mist suspended in a gas jet, having a near sonic velocity.

It has been found by the inventor that, when the delivery head 14 is held close to tissue being cleansed, typically at a distance of up to about 10 cm, the microscopic liquid droplets bombard it and all contaminants thereon, thereby to forcibly remove them from the tissue, thereby cleansing it.

The wetting of the contaminants in this way, namely, by microscopic droplets, cause a substantial increase in their aerodynamic resistance, such that the force of the bombardment by the combined fluid jet is able to separate them from the tissue surface and carry them away in the droplet stream. The increase in the aerodynamic resistance of the particles is facilitated by the wetting by droplets, on the one hand, and by the absence of a liquid stream on the tissue surface with a stable boundary layer, on the other hand. Accordingly, as none of the contaminant matter is protected by a stable boundary layer of a liquid stream, it is all exposed to removal by the gas-liquid droplet stream.

Figure 4:
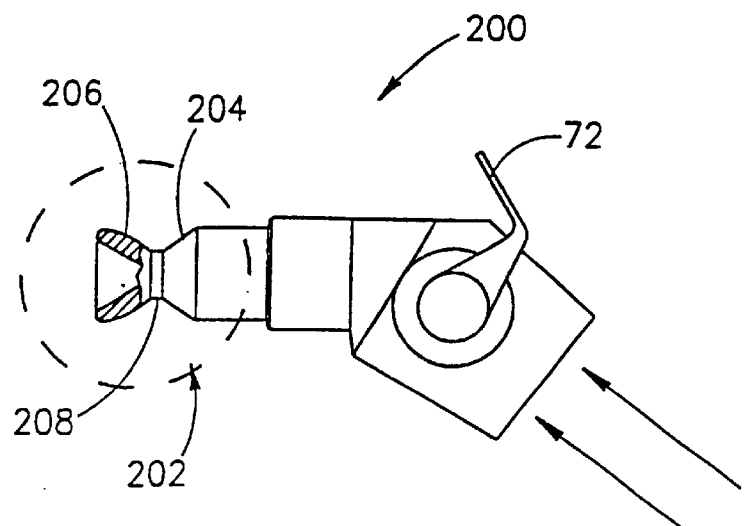
FIG. 4 is a partial side view of a fluid delivery head constructed in accordance with an alternative embodiment of the invention, and having a nozzle portion which is configured to create a suction pressure in its immediate vicinity.
Figure 5:
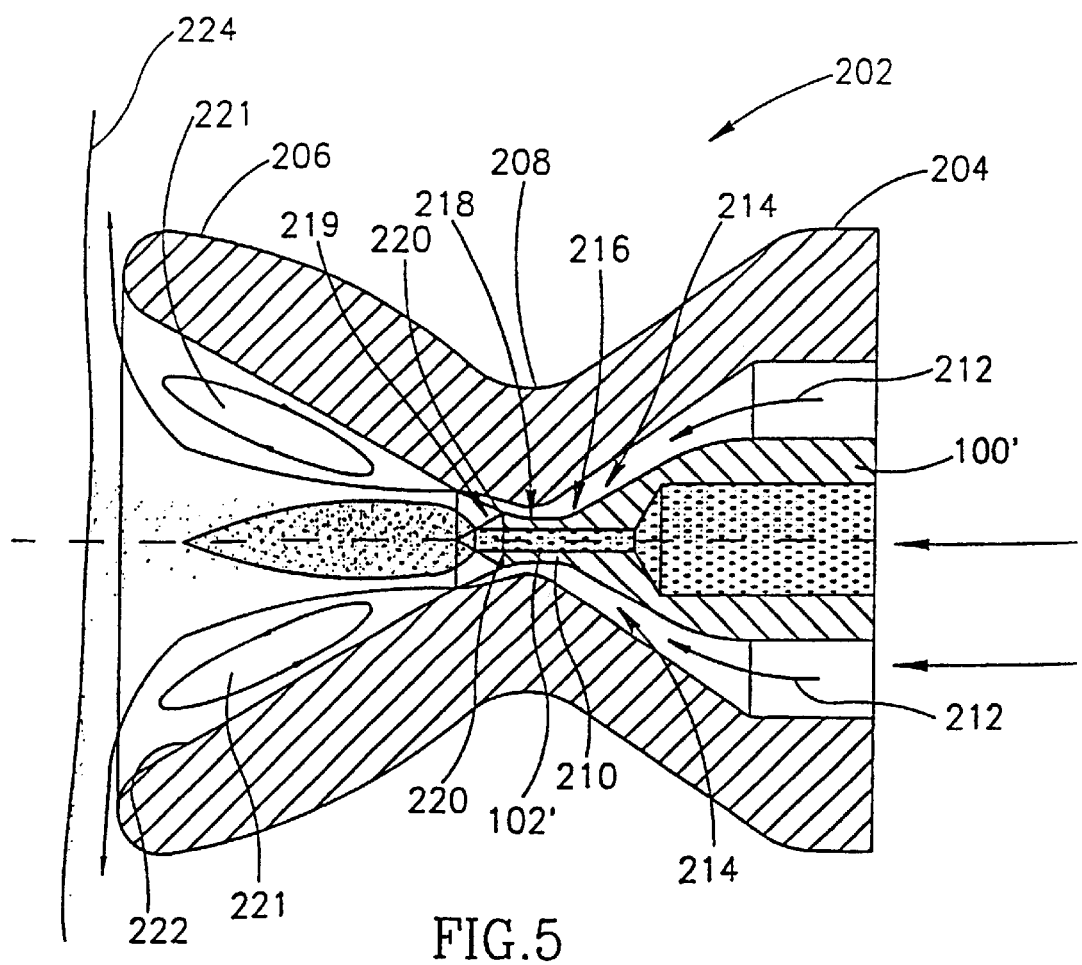
FIG. 5 is an enlarged diagrammatic side-sectional view of the nozzle of the fluid delivery head seen in FIG. 4, showing the formation of the suction pressure thereby.

Reference is now made to FIG. 4, which illustrates a fluid delivery head, referenced generally 200, and to FIG. 5, which illustrates in detail the nozzle 202 of the fluid delivery head 200, constructed in accordance with an alternative embodiment of the invention. Delivery head 200 is similar to delivery head 14, shown and described above in conjunction with FIGS. 1 and 3A, and is thus not described again herein except with regard to differences between delivery head 200 and delivery head 14. Accordingly, components of delivery head 200 seen in either of FIGS. 1 or 3A, and having counterpart components therein, are denoted in FIG. 5 by similar reference numerals but with the addition of a prime (')notation.

Referring again to FIG. 5, delivery head 200 is characterized by having a nozzle, referenced generally 202, which incorporates in a unitary member a rear, gas-liquid combining portion 204, and a front, suction portion 206. Nozzle 202 generally has an hourglass configuration, such that rear portion 204 and front portion 206 taper towards a narrow waist or transition portion 208. Inner nozzle member 100' is formed so as to protrude slightly through transition portion 208 and has a corresponding, slightly narrowed waist portion 210 whose diameter increases, as seen, as it protrudes into suction portion 206.

As a gas stream, shown by arrow 212, at superatmospheric pressure, enters the narrowing annular passageway 214 defined between inner nozzle member 100' and nozzle 202, it accelerates from a sub-sonic velocity, at the entrance 216 of the constricting passageway, to sonic velocity, at a location 218 part-way along the passageway, to supersonic velocity, at a location 219 as the constricted passageway abruptly terminates due to a step formed by front edge 220 of inner nozzle member 100'. As the gas flow emerges into the widening front nozzle portion 206 from transition zone 208, it expands rapidly. The expansion wave thus generated undergoes a considerable pressure drop, to at least subatmospheric pressure, thereby also giving rise to a conical rarefaction zone 221 along the inner surface 222 of front nozzle portion 206.

An accelerating liquid stream emerging through passing through nozzle opening 102' emerges into the supersonic gas stream, and, due to the sharp pressure drop experienced, substantially as described above in conjunction with FIGS. 1–3C, atomizes into microscopic droplets which are then swept into the gas stream, so as to form a combined gas-liquid mist stream.

When the fluid delivery head 200 is held close to tissue 224 contaminated with various pollutant particles, at a distance of, for example, 3–8 mm, these particles are exposed to the described subatmospheric pressure obtaining in the nozzle cavity. In addition to the microscopic liquid droplet bombardment as described above in conjunction with FIGS. 1–3C, therefore, the pollutant particles are also exposed to a suction force as the nozzle is brought close to the tissue being cleansed, which helps to loosen the particles from the tissue, prior to being carried away in the gas-liquid mist.

It will be appreciated by persons skilled in the art the scope of the present invention is not limited by what has been particularly shown and described above. Rather, the scope of the invention is limited solely by the claims, which follow.

What is claimed is:

1. Apparatus employing liquid and gas as working fluids for cleansing living tissue, which comprises:

a container for a sterile liquid;

a fluid delivery head having a liquid entry port and a gas entry port, fluid outlet means, and valve means located between said entry ports and said fluid outlet means and for selectably permitting respective liquid and gas flows from said entry ports to said fluid outlet means;

liquid conduit means extending between a liquid inlet located within said container and a liquid outlet connected to said liquid entry port of said delivery head;

gas conduit means extending between a gas inlet and a gas outlet, wherein said gas inlet is connected to a source of pressurized gas and said gas outlet is connected to said gas entry port of said delivery head, and wherein said gas conduit means is connected to said container via an intermediate outlet port; and means for selectably exposing said source of sterile liquid to a flow of pressurized gas flowing from said gas inlet to said gas outlet and into said gas entry port of said fluid delivery head, thereby to pump said sterile liquid along said liquid conduit means, from said inlet to said outlet, and into said liquid entry port of said fluid delivery head, wherein said fluid outlet means comprises nozzle member arranged to receive said gas and liquid flows and to combine them into a gas-liquid outflow which is operative to exit said apparatus through said fluid outlet in the form of a sterile liquid mist suspended in a high velocity gas stream.

2. Apparatus according to claim 1, wherein said gas flow exits said valve means into said gas-liquid combining member at a pressure of a first magnitude, and said combining member is operative to cause a pressure drop in the gas flow therethrough such that the pressure of the gas-liquid outflow downstream of said fluid outlet, is of a second magnitude, wherein said first magnitude is at least twice said second magnitude, so as to cause a shock wave in the gas-liquid flow downstream of said fluid outlet and atomizing of the liquid portion of said outflow into microscopic droplets, thereby to form a mist suspended in the gas portion of said outflow.

3. Apparatus according to claim 2, wherein said gas-liquid outflow, downstream of said fluid outlet, has a near-sonic velocity.

4. Apparatus according to claim 1, wherein said gas inlet of said gas conduit means is constructed for connection to a pressurized oxygen source, and said outflow is an outflow of said sterile liquid mist suspended in a high velocity oxygen stream.

5. Apparatus according to claim 2, wherein said fluid outlet means also comprises means for applying a suction force to the tissue being cleansed.

6. Apparatus according to claim 2, wherein said fluid outlet means further comprises an interior nozzle member arranged to provide an outflow of sterile liquid, and said nozzle member comprises:

a rear portion configured to fit over said interior nozzle member and arranged to fit over said interior nozzle member so as to define a passageway therebetween for said gas flow;

a waist portion defined by a forward tapering of said rear portion;

a front portion defining an opening and tapering rearwardly towards said waist portion, wherein said passageway is formed so as to be increasingly constricted towards said front portion of said nozzle, such that said gas flow passing through said passageway is accelerated to at least sonic velocity, and wherein said front portion widens towards said opening thereof such that said accelerated gas flow expands and thus undergoes a drop to a pressure which is subatmospheric, such that, when said nozzle opening is brought close to tissue contaminated by pollutant particles, the particles are exposed to said subatmospheric pressure so as to be loosened thereby from the tissue.

7. Apparatus according to claim 1, wherein said delivery head is configured to be used while being held in one hand.

8. A method of cleansing living tissue, which comprises:

exposing a source of sterile liquid to a flow of pressurized gas, thereby to cause a pumped supply thereof into a fluid delivery head;

supplying the pressurized gas to the fluid delivery head;

wherein the step of supplying the pressurized gas includes supplying the gas at a pressure of a first magnitude; and combining the gas and liquid supplied to the delivery head in such a manner as to cause a pressure drop in the gas flow such that the pressure of the gas-liquid outflow, is of a second magnitude, wherein said first magnitude is at least twice said second magnitude, so as to cause a shock wave in the gas-liquid outflow and atomizing of the liquid portion of the outflow into microscopic droplets, thereby to form a mist suspended in the gas portion of the outflow so as to provide a gas-liquid outflow in the form of a sterile liquid mist suspended in a high velocity gas stream; and exposing the living tissue to the gas-liquid outflow, thereby to remove therefrom contaminants and to wet the living tissue.

9. A method according to claim 8, and further comprising the steps, prior to said step of combining, of:

providing a gas outflow;

causing an expansion of the gas outflow, thereby to cause a reduction in the pressure thereof to subatmospheric pressure, thereby provide a suction force; and providing a liquid outflow in conjunction with said expanded gas outflow.

10. A method according to claim 8 wherein the gas-liquid outflow has a near-sonic velocity.

11. A method according to claim 8, wherein the pressurized gas is oxygen.

12. A method of cleansing living tissue, which includes:

exposing a source of sterile liquid to a flow of pressurized oxygen, thereby to cause a pumped supply thereof into a fluid delivery head and supplying the pressurized gas to the fluid delivery head;

wherein the step of supplying the pressurized gas includes supplying the gas at a pressure of a first magnitude; and combining the gas and liquid supplied to the delivery head in such a manner as to cause a pressure drop in the gas flow such that the pressure of the gas-liquid outflow, is of a second magnitude, wherein said first magnitude is at least twice said second magnitude, so as to cause a shock wave in the gas-liquid outflow and atomizing of the liquid portion of the outflow into microscopic droplets, thereby to form a mist suspended in the gas portion of the outflow so as to provide a gas-liquid outflow in the form of a sterile liquid mist suspended in a high velocity gas stream; and exposing the living tissue to the gas-liquid outflow, thereby to remove therefrom contaminants and to wet the living tissue.

13. A method according to claim 9 wherein the gas-liquid outflow has a near-sonic velocity.

* * * * *